United States Patent
Sievers et al.

(10) Patent No.: US 6,274,749 B1
(45) Date of Patent: Aug. 14, 2001

(54) HIGH-TEMPERATURE RESISTANT SULFONATED AROMATIC POLYETHER KETONE CATION EXCHANGERS AND SULFONATED POLY (PHENYLENE SULFIDE) CATION EXCHANGERS AS CATALYSTS AT REACTION TEMPERATURE ABOVE 150° C

(75) Inventors: Werner Sievers; Ulrich Daiminger, both of Frankfurt; Harald Bönsel, Waldems; Wolfgang Bauer, Hattersheim; Joachim Semel, Königstein, all of (DE)

(73) Assignee: Hoechst Research & Technology GmbH & Co. KG, Frankfurt am Main (DE)

( * ) Notice: Subject to any disclaimer, the term of this patent is extended or adjusted under 35 U.S.C. 154(b) by 0 days.

(21) Appl. No.: 09/121,238

(22) Filed: Jul. 23, 1998

(30) Foreign Application Priority Data

Jul. 29, 1997 (DE) .............................. 197 32 578

(51) Int. Cl.[7] .............................. B01J 31/00; C07C 51/00
(52) U.S. Cl. .............................. 554/170; 502/159
(58) Field of Search .............................. 502/159; 554/170

(56) References Cited

U.S. PATENT DOCUMENTS

| | | | |
|---|---|---|---|
| 3,553,238 | * 1/1971 | Cenker | 554/170 |
| 4,125,549 | * 11/1978 | Coopersmith et al. | 554/170 |
| 4,548,754 | * 10/1985 | Day et al. | 554/170 |
| 4,652,406 | * 3/1987 | Lepper et al. | 554/170 |
| 5,362,836 | * 11/1994 | Helmer-Metzmann et al. | 528/125 |
| 5,371,253 | 12/1994 | Cooper . | |
| 5,426,199 | * 6/1995 | Lundquist | 554/170 |
| 5,438,082 | 8/1995 | Helmer-Metzmann et al. . | |
| 5,536,856 | * 7/1996 | Harrison et al. | 554/170 |
| 6,096,856 | * 8/2000 | Helmer-Metzmann et al. | 528/374 |

FOREIGN PATENT DOCUMENTS

| | | | |
|---|---|---|---|
| 40 27 639 | * 3/1992 | (DE) | 554/170 |
| 195 10 026 | * 9/1996 | (DE) . | |
| 195 27 435 | 1/1997 | (DE) . | |
| 0 575 807 | * 12/1993 | (EP) . | |
| 0574791 | 12/1993 | (EP) . | |
| WO 96/13073 | 5/1996 | (WO) . | |
| WO 96/29360 | * 9/1996 | (WO) . | |
| WO 97/19480 | 5/1997 | (WO) . | |

OTHER PUBLICATIONS

T.R.E. Kressman, Chemistry and Industry, pp. 64–69, Jan. 1956.*

Ullmann's Encyclopedia of Industrial Chemistry, 6th ed., High–Temperature Polymers—Introduction; Polyaryletherketones; Poly(phenylene sulfide), 2000.*

Y. Z. Yuan et al., Chinese Chemical Letters, vol. 4, No. 2, pp. 163–166, 1993.

* cited by examiner

Primary Examiner—Mark L. Bell
Assistant Examiner—J. Pasterczyk
(74) Attorney, Agent, or Firm—Frommer Lawrence & Haug LLP

(57) ABSTRACT

High-temperature resistant sulfonated aromatic polyether ketone cation exchangers and sulfonated poly(phenylene sulfide) cation exchangers are revealed as catalysts for various reactions at reaction temperatures above 150° C.

The invention relates to the use of sulfonated aromatic polyether ketone cation exchangers and sulfonated poly(phenylene sulfide) cation exchangers as catalysts for such reactions. The preferred reaction is esterification to make octyl palmitate.

5 Claims, 1 Drawing Sheet

Diagram 1: Plot of absolute capacities

Diagram 2: Plot of normalized capacities

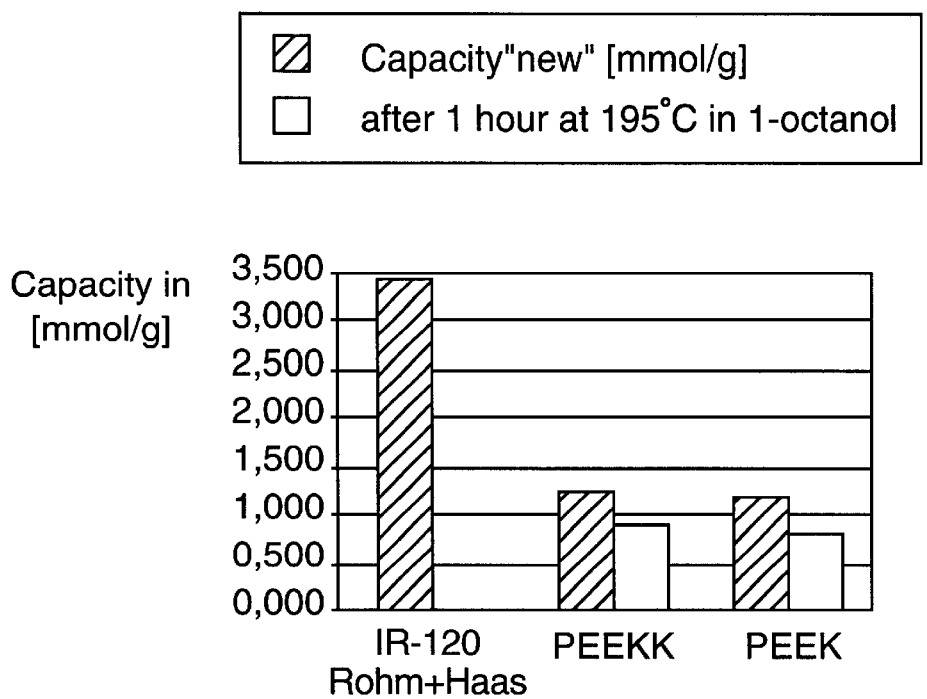
Diagram 1: Plot of absolute capacities
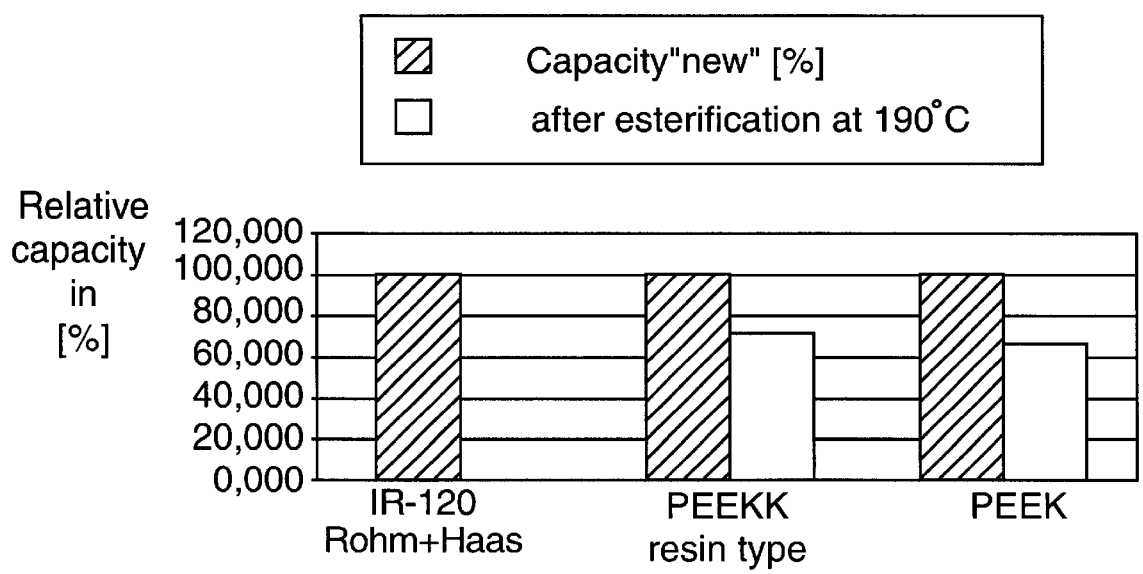
Diagram 2: Plot of normalized capacities

HIGH-TEMPERATURE RESISTANT SULFONATED AROMATIC POLYETHER KETONE CATION EXCHANGERS AND SULFONATED POLY (PHENYLENE SULFIDE) CATION EXCHANGERS AS CATALYSTS AT REACTION TEMPERATURE ABOVE 150° C

DESCRIPTION OF THE FIGURES.

In the following Description reference will be made to the accompanying drawing, wherein, FIG. 1 is a bar chart showing the absolute exchange capacities of the listed resins; and FIG. 2 is a bar chart showing the normalized exchange capacities of the listed resins measured before and after an esterification reaction.

High-temperature resistant sulfonated aromatic polyether ketone cation exchangers and sulfonated poly(phenylene sulfide) cation exchangers as catalysts at reaction temperatures above 150° C.

Acidic cation exchangers which are distinguished by a very high heat stability have been prepared on the basis of aromatic polyether ketones and poly(phenylene sulfide)s according to EP 0 575 807 A1, EP 0 574 791 A2, DE 195 10 026 A1 and DE 195 27 435.0 which is expressly incorporated herein by reference. Temperatures up to 240° C. are permissible as a long-term load, peak temperatures up to 280° C. are possible as a short-term load. The extremely high heat stability results from the use of the above-described starting materials and the special preparation process. Acidic cation exchange resins offered on the market are principally prepared on the basis of crosslinked styrene-divinylbenzene or acrylic and have a maximum working temperature of 150° C. They are usually used as proton-conducting membranes, for example in fuel cells. WO 97/19480 A1 and EP 0 574 791 A2 further disclose catalysts which comprise aromatic polyether ketones, but not as catalytically active materials.

It has now surprisingly been found that sulfonated aromatic polyether ketone cation exchangers and sulfonated poly(phenylene sulfide) cation exchangers may be used in a technical field other than that mentioned, that is to say as catalysts in heterogeneously acid-catalyzed reactions. This is all the more surprising, since to date there have been no acidic ion exchangers based on organic monomers.

The invention therefore relates to the use of sulfonated aromatic polyether ketone cation exchangers and sulfonated poly(phenylene sulfide) cation exchangers as catalysts.

In contrast to homogeneously catalyzed reactions, in the case of heterogeneously catalyzed reactions, the site of the reaction can be precisely defined and, furthermore, the removal, work-up and recycling of the catalyst is not required. On account of physicochemical or economic reasons, in the case of numerous heterogeneously catalyzed reactions, furthermore, a high working temperature is fundamentally necessary or at least highly advantageous. It is generally known that chemical reactions are accelerated, or are made possible at all, by high temperatures. Typical examples of such reactions are esterifications/ester cleavage, etherifications/ether cleavage, acetylization/acetal cleavage, eliminations/hydratization, and alkylations. In all these acid-catalyzed processes, said high-temperature resistant ion exchangers can be used advantageously. This is independent of the type of apparatus, which can be designed as a kettle reactor, tubular reactor, etc. A further surprising advantage of acidic cation exchangers based on aromatic polyether ketones and poly(phenylene sulfide)s results, that owing to the possible adjustment of the degree of ion exchanger equivalents, reactions at high temperatures can be selectively accelerated: thus in carboxylic acid/alcohol mixtures at high temperatures at low sulfonation degrees the esterification is preferentially catalyzed, and at higher sulfonation degrees the etherification of the alcohols present is preferentially catalyzed. Furthermore, the high-temperature resistant cation exchangers can be used in processes, such as reactive distillation, in which mass transfer of the individual product proceeds simultaneously with the reaction. In this case also, marked advantages of high-temperature resistant cation exchangers are demonstrated, since temperatures above 150° C. are frequently required precisely in the combined mass transfer by rectification.

The cation exchangers for the use according to the invention can be prepared in the following manner: the aromatic polymer is dissolved in 94–97% by weight sulfuric acid and the solution is admixed with a sulfonating agent, e.g. oleum, until the sulfuric acid concentration is 98–99.9% by weight. When the desired degree of sulfonation is achieved, the reaction batch is worked up. Poly(phenylene sulfide) is sulfonated in a mixture of oleum and chlorosulfonic acid. Up to ion exchanger equivalents of 1.0 mmol of $SO_3H/g$, the materials are produced as powders insoluble in NMP (N-methyl-2-pyrrolidone). From ion-exchanger equivalents of 1.0 mmol of $SO_3H/g$, the polymers are soluble in NMP or DMSO (dimethyl sulfoxide). If the degree of sulfonation is increased further, the polarity of the polymer increases, and from an ion-exchanger equivalent of 1.8 mmol of $SO_3H/g$, the material is water-soluble.

These high-temperature resistant ion exchangers show, as derivatives of high-performance polymers, outstandingly high chemical and thermal resistance. According to DSC and TGA studies, at heating rates of 10° C./min, thermal desulfonation cannot be observed until above 300° C.

The example below serves for further explanation of the invention. No restriction of the invention in any manner is intended thereby.

The example of the esterification of palmitic acid to form octyl palmitate is to show the advantageous use of the novel high-temperature resistant cation exchangers in comparison with the products available on the market. The acid-catalyzed reaction of palmitic acid (boiling point 350° C.) and octanol (boiling point 195° C.) to form octyl palmitate and water was carried out at 200° C. at atmospheric pressure in a stirred vessel. 265 grams of octanol and 522 grams of palmitic acid were introduced into the heatable stirred tank. After heating the tank to 190–195° C. by means of an oil thermostat, 100 grams of the respective ion exchanger were added in powder or granule form. The vapors passing overhead, in this case the water vapor produced as product, are condensed in a Liebig condenser and collected in a receiver standing on a balance.

The catalysts used were: a high-temperature resistant cation exchange resin based on PEEKK (polyether ether ketone ketone), a high-temperature resistant cation exchange resin based on PEEK (polyether ether ketone), a cation exchanger available on the market type IR120, from Rohm and Haas.

The resin IR120 is not identical to, but comparable with, the HCR-S type from Dow Chemicals, type S100 from Bayer, type CF from Mitsubishi Chemicals and type C100 from Purolite.

A quantitative measure of the advantage of the process according to the invention is the retention of catalytic activity under the extreme conditions studied. A measure which can be taken from this is the exchange capacity of the cation exchanger, since this is fundamentally responsible for the catalytic action. Therefore, the exchange capacities of the resins were each measured before and after the esterification reaction. In this instance, the resin was dried in advance in a vacuum drying cabinet at 80° C. and weighed, so that the following capacity data relate to the dry mass. The capacity itself is measured as exchange capacity of protons against sodium ions. After a residence time of one hour in the stirred vessel, the following capacities of the resins were measured: High-temperature resistant cation exchanger based on PEEKK: before esterification 1.232 mmol of $SO_3H$/g, after esterification 0.897 mmol of $SO_3H$/g (equivalent to 73% of the original capacity). High-temperature resistant cation exchanger based on PEEK: before the esterification 1.169 mmol of $SO_3H$/g, after the esterification 0.793 mmol of $SO_3H$/g (equivalent to 68% of the original capacity).

Cation exchanger IR120: before esterification 3.440 mmol of $SO_3H$/g, after the esterification: 0.03 mmol of $SO_3H$/g (equivalent to 1% of the original capacity)

What is claimed is:

1. A method of catalyzing a chemical reaction, comprising esterification at a temperature in the range of 20–300° C., which comprises, adding to the reactants of the reaction a cation exchange resin catalyst in acidic form selected from the group consisting of an aromatic polyether ketone cation exchanger and a sulfonated poly(phenylene sulfide) cation exchanger.

2. The method as claimed in claim 1 wherein the aromatic polyetherketone cation exchanger and sulfonated poly (phenylene sulfide) cation exchanger are used as catalysts is heterogeneous or acid catalysis in the esterification reaction.

3. The method as claimed in claim 1 wherein the reaction takes place at temperatures from the range 150–280° C.

4. The method as defined in claim 4 wherein the reaction is an esterification reaction which involves reacting palmitic acid with octanol to obtain octyl palmitate.

5. The method as claimed in claim 4 wherein said catalyst is selected from the group consisting of a cation exchange resin in acidic form selected from the group consisting of a polyether etherketone ketone and a polyether ether ketone.

* * * * *